(12) United States Patent
Lewandowski et al.

(10) Patent No.: US 9,656,244 B2
(45) Date of Patent: May 23, 2017

(54) PROCESS FOR THE PRODUCTION OF 1,3-BUTADIENE

(71) Applicant: SYNTHOS S.A., Oswiecim (PL)

(72) Inventors: Marek Lewandowski, Katowice (PL); Agnieszka Ochenduszko, Tychy (PL); Matthew Jones, Bristol (GB)

(73) Assignee: SYNTHOS S.A., Oswiecim (PL)

( * ) Notice: Subject to any disclaimer, the term of this patent is extended or adjusted under 35 U.S.C. 154(b) by 0 days.

(21) Appl. No.: 14/889,644

(22) PCT Filed: May 5, 2014

(86) PCT No.: PCT/EP2014/059092
§ 371 (c)(1),
(2) Date: Nov. 6, 2015

(87) PCT Pub. No.: WO2014/180778
PCT Pub. Date: Nov. 13, 2014

(65) Prior Publication Data
US 2016/0082417 A1    Mar. 24, 2016

(30) Foreign Application Priority Data
May 7, 2013    (EP) .................................... 13461530

(51) Int. Cl.
| C07C 1/20 | (2006.01) |
| C07C 1/24 | (2006.01) |
| B01J 23/06 | (2006.01) |
| B01J 23/10 | (2006.01) |
| B01J 37/08 | (2006.01) |
| B01J 37/02 | (2006.01) |

(52) U.S. Cl.
CPC ........... *B01J 23/10* (2013.01); *B01J 37/0201* (2013.01); *B01J 37/08* (2013.01); *C07C 1/20* (2013.01); *C07C 1/24* (2013.01); *B01J 2523/00* (2013.01); *C07C 2521/06* (2013.01); *C07C 2521/08* (2013.01); *C07C 2523/06* (2013.01); *C07C 2523/10* (2013.01)

(58) Field of Classification Search
None
See application file for complete search history.

(56) References Cited

U.S. PATENT DOCUMENTS

2,436,125 A       2/1948  Spence et al.
6,323,383 B1 *   11/2001  Tsuchida .............. B01J 27/1806
                                                                44/300

FOREIGN PATENT DOCUMENTS

| JP | 2005-206472 | 8/2005 |
| JP | 2006-218395 | 8/2006 |
| RU | 007871 | 2/2007 |
| WO | WO 94/21376 | 9/1994 |
| WO | WO 99/38822 | 8/1999 |
| WO | WO 03/074177 | 9/2003 |
| WO | WO 2012/015340 | 2/2012 |

OTHER PUBLICATIONS

International Preliminary Report on Patentability issued in PCT/EP2014/059092 dated Nov. 10, 2015.
International Search Report for PCT/EP2014/059092, mailed Aug. 25, 2014, 3 pages.
Jones et al., "Investigations into the conversion of ethanol into 1,3-butadiene", Catalysis Science & Technology, vol. 1, No. 2, Jan. 2011, pp. 267-272.
Boukha et al., "Influence of the calcination temperature on the nano-structural properties, surface basicity, and catalytic behavior of alumina-supported lanthana samples," *Journal of Catalysis*, vol. 272: 121-130 (2010).
Frey et al., "Supported $La_2O_3$ and MgO Nanoparticles as Solid Base Catalysts for Aldol Reactions While Suppressing Dehydration at Room Temperature," *ChemCatChem*, vol. 5: 594-600 (2013).
Chinese Office Action issued in App. No. 201480026031.2 dated Aug. 25, 2016 (w/ English Summary).
Japanese Office Action issued in App. No. 2016-512316 dated Oct. 11, 2016.

\* cited by examiner

*Primary Examiner* — In Suk Bullock
*Assistant Examiner* — Philip Louie
(74) *Attorney, Agent, or Firm* — Nixon & Vanderhye P.C.

(57) ABSTRACT

The invention relates to the use of a novel silica-supported trimetallic (La/Zr/Zn) catalyst in the production of 1,3-butadiene from ethanol. The presence of lanthanum in the catalyst further comprising zirconium and zinc increases the catalyst's yield and selectivity to 1,3-butadiene.

8 Claims, No Drawings

PROCESS FOR THE PRODUCTION OF 1,3-BUTADIENE

This application is the U.S. national phase of International Application No. PCT/EP2014/059092 filed 5 May 2014, which designated the U.S. and claims priority to EP Patent Application No. 13461530.1 filed 7 May 2013, the entire contents of each of which are hereby incorporated by reference.

The invention relates to a process for the production of 1,3-butadiene from a feed comprising ethanol in the presence of a trimetallic catalyst. The catalyst comprises lanthanum, zirconium and zinc on a silica support. Furthermore, the present invention relates to a method for preparation of a novel supported catalyst, and the supported catalyst. Finally, the invention relates to the use of lanthanum in a catalyst for the production of 1,3-butadiene from ethanol, to increase the selectivity of the catalytic reaction, the catalyst further comprising zirconium and zinc.

1,3-Butadiene is a commodity chemical and is of considerable interest for the production of synthetic rubbers. It is presently mainly produced from non-sustainable sources. The catalytic synthesis of 1,3-butadiene from a renewable source, ethanol, has also previously been disclosed. Most recently, M. D. Jones et al. (*Catal. Sci. Technol.*, 2011, 1, 267-272) describe a study of bimetallic and trimetallic catalysts. Particularly promising results are reported for the system $ZrO_2/ZnO$. Salts of Zn and Zr were impregnated onto a variety of support materials, and the resulting catalyst precursors were calcined to generate the respective metal oxides. The trimetallic system Cu/Zr/Zn on a 150 Å silica is reported to have the highest selectivity to 1,3-butadiene, albeit with a lower conversion than some of the Zr/Zn catalysts without Cu. With this specific trimetallic catalyst, and unlike with other catalysts, addition of acetaldehyde to the feed did not result in a significant enhancement of the selectivity to 1,3-butadiene. The trimetallic catalyst on 60 Å silica showed a drop in selectivity to 1,3-butadiene with time.

WO 2012/015340 A1 illustrates a one-step process for the production of 1,3-butadiene from a feed comprising ethanol and optionally acetaldehyde in the presence of a catalyst containing metals selected from the group silver, gold or copper, and metal oxide selected from the group of magnesium, titanium, zirconium, and tantalum oxides, optionally modified with alkali metals and/or cerium, tin or antimony oxides.

JP 2005/206472 A and JP 2006/218395 A relate to the preparation of nitriles from organic compounds by ammoxidation.

There is a continuing need for processes for the production of 1,3-butadiene having increased selectivity and/or conversion.

SUMMARY OF THE INVENTION

According to the present invention, it was surprisingly found that a catalyst comprising lanthanum, zirconium and zinc as catalytic metals on a support comprising silica gives favourable conversion and selectivity to 1,3-butadiene.

Thus, in a first aspect, the present invention relates to a process for the production of 1,3-butadiene, the process comprising i) providing a supported catalyst comprising lanthanum, zirconium, and zinc, the support comprising silica; and ii) contacting a feed comprising ethanol with the supported catalyst, to obtain a raw product comprising 1,3-butadiene.

In a second aspect, the present invention relates to a method for preparation of a supported catalyst, the method comprising a) impregnating a support comprising silica with a salt of lanthanum, b) drying the impregnated support of step a), and c) calcining the dried impregnated support of step b). The supported catalyst of the invention in addition to lanthanum further comprises zirconium and zinc.

Moreover, and in a third aspect, the invention relates to the supported catalyst as produced, or producible, according to the method of the second aspect.

Finally, and in a fourth aspect, the invention relates to the use of lanthanum in a process for the production of 1,3-butadiene from a feed comprising ethanol and optionally acetaldehyde, to increase the selectivity of the catalytic reaction to 1,3-butadiene, the catalyst further comprising zirconium and zinc.

DETAILED DESCRIPTION OF THE INVENTION

1) Method for Preparation of the Supported Catalyst

As set out above, the invention relates to a method for preparation of a supported catalyst comprising steps a) to c). In step a), a support comprising silica is impregnated with a salt of lanthanum. In step b), the impregnated support of step a) is dried. In step c), the dried impregnated support of step b) is calcined.

In one preferred embodiment, the method of the invention comprises additional steps, namely
 d) impregnating the calcined dried impregnated support of step c) with a salt of zirconium and a salt of zinc;
 e) drying the impregnated support of step d); and
 f) calcining the dried impregnated support of step e,
i.e. this preferred method is a two-step impregnation method.

In an alternative preferred embodiment of the method according to the invention, the support is impregnated in step a) with a salt of lanthanum, a salt of zirconium, and a salt of zinc, i.e. it is a one-step impregnation method.

Suitable salts of lanthanum are e.g. inorganic acid salts of lanthanum, preferably inorganic acid salts of La(III). Preferred inorganic acids are selected from sulphuric acid, nitric acid and hydrochloric acid, and La(III) nitrates are even more preferred. Most preferable, the lanthanum salt as used in step (a) is La(III) nitrate hexahydrate, $La(NO_3)_3 \cdot 6H_2O$.

With respect to the salt of zirconium used in the method for preparation of the supported catalyst, suitable salts are e.g. organic or inorganic acid salts of zirconium, preferably of Zr(IV). Preferred inorganic acids are selected from sulphuric acid, nitric acid and hydrochloric acid. Most preferred are zirconium salts such as $Zr(O_2CCH_3)_4$ and $ZrO(NO_3)_2 \cdot xH_2O$. The use of the acetylacetonate salt, $Zr(C_2H_7O_2)_4$, is also preferred.

With respect to the salt of zinc used in the method for preparation of the supported catalyst, suitable salts are e.g. organic and inorganic acid salts of zinc. Most preferred salts are $Zn(NO_3)_2 \cdot 6H_2O$ and $Zn(O_2CCH_3)_2 \cdot 6H_2O$.

2) Supported Catalyst

The supported catalyst of the invention comprises lanthanum, zirconium, and zinc. It is supported on a silica support, i.e. a support comprising silica.

With respect to the amount of lanthanum, a preferred range in all aspects of the invention is 0.1 to 20% by weight, calculated as La metal on support, preferably 0.5 to 10% by weight, in particular 1 to 5% by weight, such as 2.0 to 3.0% by weight.

Preferred amounts of zirconium according to all aspects of the invention are 0.1 to 5% by weight, calculated as Zr metal on support, preferably 0.5 to 3% by weight, in particular 1 to 2% by weight, such as 1.5% by weight.

Preferred amounts of zinc according to all aspects of the invention are 0.05 to 3% by weight, calculated as Zn metal on support, preferably 0.1 to 2% by weight, in particular 0.3 to 1.0% by weight, such as 0.5% by weight.

The support of the supported catalyst of all aspects of the invention comprises silica. In addition to silica, the support may comprise of ceria, magnesia or alumina. It is most preferred that the support is (i.e. essentially consists of) silica. Suitable catalyst supports are e.g. $SiO_2$ with BET surface areas in a range of from 50 to 800 $m^2g^{-1}$. Preferred are silicas having a pore diameter in a range of from 40 to 2000 Å, preferably 100 to 600 Å, in particular 150 to 500 Å.

In the most preferred embodiment, the supported catalyst is produced or producible according to the method of the first aspect of the invention.

3) Process for the Production of 1,3-Butadiene

The process for the production of 1,3-butadiene of the invention comprises the following steps
i) providing a supported catalyst comprising lanthanum, zirconium, and zinc, the support comprising silica; and
ii) contacting a feed comprising ethanol with the supported catalyst, to obtain a product comprising 1,3-butadiene.

Preferably, the contacting ii) takes place at a temperature in a range of from 200 to 600° C., preferably 300 to 425° C. Also, it is preferred that contacting ii) takes place at a weight hourly space velocity of 0.2 to 7 $h^{-1}$.

The gaseous feed can contain 85 to 98% by volume of ethanol, preferably 90 to 95% by volume, such as about 92% by volume (with the rest of this raw ethanol being water). The process according to the invention is, however, preferably characterized in that the gaseous feed in addition to ethanol comprises acetaldehyde. As shown in the examples, and unlike with the trimetallic Cu/Zr/Zn silica catalyst reported in *Catal. Sci. Technol.*, 2011, 1, 267-272, the presence of moderate amounts of acetaldehyde in the feed increases the selectivity of the reaction to 1,3-butadiene.

Thus, the feed preferably comprises up to 40% by volume, more preferred up to 30% by volume, in particular up to 20% by volume of acetaldehyde.

The process according to the invention preferably further comprises
iii) separating the raw product into a first portion comprising 1,3-butadiene and a second portion comprising acetaldehyde.

It is most preferred in the process according to the invention that at least part of the second portion as obtained in step iii) is added to the feed, i.e. that at least part of the acetaldehyde produced is recycled into the feed.

The following examples show the advantages of the present invention. Unless noted otherwise, all percentages are given by weight.

EXAMPLES

1. Preparation of Supported Catalysts

The preparation of the supported catalysts for Examples 1 to 4 and 5 to 10, respectively, was conducted as follows:

1a) Examples 1 to 4, and 11

Examples 1 and 11 constitute the control catalyst described in Jones et al. (*Catal. Sci. Technol.*, 2011). In Examples 2-4, lanthanum (using the nitrate of lanthanum as a salt) was added together with appropriate amounts of Zr(IV) and Zn(II) in one step of impregnation. After impregnation, the impregnated support was dried and calcined with a heating ramp of 5° C./min until at 500° C., and was held at this temperature for 5 hours.

1b) Examples 5 to 10 and 12 to 28

Preparation of the supported catalyst was carried out by two separate steps of impregnation: First, silica was impregnated with appropriate amounts of lanthanum using the nitrate of lanthanum as a salt. After impregnation, the impregnated support was dried and calcined with a heating ramp of 5° C./min until at 500° C., and was held at this temperature for 5 hours. The next step was the impregnation with salts of Zr(IV) and Zn(II), drying and calcination with a heating ramp of 5° C./min until at 500° C. The supported catalyst was held at this temperature for 5 hours.

2. Catalytic Tests

The catalytic tests were carried out under a gas phase at 325 to 375° C., under atmospheric pressure with weight hourly space velocities (WHSV) in a range of 0.3 to 5 $h^{-1}$. The feedstock was either 96% by volume of ethanol and 4% by volume of water (Examples 1 to 12), 92% by volume of ethanol and 8% by volume of water (Examples 13 and 17), or a mixture of this purity of ethanol (92% by volume of ethanol and 8% by volume of water) with acetaldehyde, in a volume ratio of raw ethanol to acetaldehyde of 9 to 1 (Examples 14, 16, 19 to 23), 8 to 2 (Examples 15 and 24 to 27), and 7 to 3 (Example 28), as indicated in the table. The carrier gas used was argon. The reaction was carried out over 3-4 hours, and the results obtained after this period are indicated in the table below.

TABLE 1

| | | | | | | | | | Results[5] | |
| | Catalyst | | | Conditions | | | | | Sel. to | Sel. to |
| Ex. | comp. [wt %] [1] | T [° C.] | WHSV[2] [$h^{-1}$] | AA/ET[3] | t [h] | PoreØ [Å] | ET[4] comp. | Conv. [%] | 1,3BTD [%] | 1,3BTD + AA [%] |
|---|---|---|---|---|---|---|---|---|---|---|
| 1 | ZrZn | 375 | 5.25 | 0 | 3 | 500 | 96 | 21 | 5 | 88 |
| 2 | ZrZn—La (0.5%) | 375 | 5.25 | 0 | 3 | 500 | 96 | 13 | 10 | 89 |
| 3 | ZrZn—La (1%) | 375 | 5.25 | 0 | 3 | 500 | 96 | 22 | 16 | 87 |
| 4 | ZrZn—La (5%) | 375 | 5.25 | 0 | 3 | 500 | 96 | 15 | 10 | 95 |
| 5 | ZrZn—La (0.5%) | 375 | 5.25 | 0 | 3 | 500 | 96 | 12 | 12 | 90 |
| 6 | ZrZn—La (1%) | 375 | 5.25 | 0 | 3 | 500 | 96 | 30 | 15 | 88 |
| 7 | ZrZn—La (2%) | 375 | 5.25 | 0 | 3 | 500 | 96 | 12 | 24 | 88 |

TABLE 1-continued

| Ex. | Catalyst comp. [wt %][1] | Conditions T [°C.] | WHSV[2] [h⁻¹] | AA/ET[3] | t [h] | PoreØ [Å] | ET[4] comp. | Results[5] Conv. [%] | Sel. to 1,3BTD [%] | Sel. to 1,3BTD + AA [%] |
|---|---|---|---|---|---|---|---|---|---|---|
| 8  | ZrZn—La (3%)  | 375 | 5.25 | 0   | 3 | 500 | 96 | 12 | 19 | 91 |
| 9  | ZrZn—La (5%)  | 375 | 5.25 | 0   | 3 | 500 | 96 | 14 | 15 | 92 |
| 10 | ZrZn—La (10%) | 375 | 5.25 | 0   | 3 | 500 | 96 | 26 | 16 | 92 |
| 11 | ZrZn          | 325 | 0.3  | 0   | 4 | 500 | 96 | 43 | 27 | 39 |
| 12 | ZrZn—La (3%)  | 325 | 0.3  | 0   | 4 | 500 | 96 | 42 | 70 | 79 |
| 13 | ZrZn—La (3%)  | 325 | 0.3  | 0   | 4 | 150 | 92 | 21 | 68 | 76 |
| 14 | ZrZn—La (3%)  | 325 | 0.3  | 1/9 | 4 | 150 | 92 | 24 | 71 | 78 |
| 15 | ZrZn—La (3%)  | 325 | 0.3  | 2/8 | 4 | 150 | 92 | 21 | 74 | 80 |
| 16 | ZrZn—La (2%)  | 325 | 0.3  | 1/9 | 4 | 150 | 92 | 17 | 73 | 79 |
| 17 | ZrZn—La (2%)  | 325 | 0.3  | 0   | 4 | 150 | 92 | 33 | 62 | 73 |
| 19 | ZrZn—La (2%)  | 340 | 0.3  | 1/9 | 4 | 150 | 92 | 17 | 71 | 77 |
| 20 | ZrZn—La (3%)  | 340 | 0.3  | 1/9 | 4 | 250 | 92 | 36 | 65 | 72 |
| 21 | ZrZn—La (3%)  | 340 | 0.45 | 1/9 | 4 | 250 | 92 | 29 | 62 | 77 |
| 22 | ZrZn—La (3%)  | 360 | 0.3  | 1/9 | 4 | 250 | 92 | 39 | 65 | 73 |
| 23 | ZrZn—La (3%)  | 360 | 0.45 | 1/9 | 4 | 250 | 92 | 34 | 60 | 75 |
| 24 | ZrZn—La (3%)  | 340 | 0.3  | 2/8 | 4 | 250 | 92 | 36 | 68 | 79 |
| 25 | ZrZn—La (3%)  | 340 | 0.45 | 2/8 | 4 | 250 | 92 | 23 | 66 | 82 |
| 26 | ZrZn—La (3%)  | 360 | 0.3  | 2/8 | 4 | 250 | 92 | 41 | 66 | 77 |
| 27 | ZrZn—La (3%)  | 360 | 0.45 | 2/8 | 4 | 250 | 92 | 31 | 61 | 78 |
| 28 | ZrZn—La (3%)  | 340 | 0.3  | 3/7 | 4 | 250 | 92 | 23 | 69 | 81 |

ET = ethanol
AA = acetaldehyde
1,3BTD = 1,3-butadiene
Comp. = composition
Conv. = conversion
Sel. = selectivity

[1] 1.5 wt % Zr and 0.5 wt % Zn on SiO$_2$. The percentages indicated are the amount of La [wt %]. The numbers are weight % of metal on support. It is believed that the metals are actually present in the active catalyst in their oxide forms ZnO, ZrO$_2$, and La$_2$O$_3$.
[2] Weight hourly space velocity.
[3] The acetaldehyde/ethanol ratio indicated is the volume ratio.
[4] 92% means 92% by volume of ethanol and 8% by volume of H$_2$O. The 2:8 volume ratio then means 20 volume % of acetaldehyde, 73.6 volume % of ethanol, and 6.4 volume % of H$_2$O etc.
[5] Conversion and selectivity were calculated in accordance with the method given by Jones et al. (*Catal. Sci. Technol.*, 2011, 1, 267-272). In all cases, the carbon balance was found to be satisfactory.

Comparing Examples 1 to Examples 2-10 shows that the addition of lanthanum to the silica-supported Zr/Zn catalyst increases the selectivity to 1,3-butadiene. The same can be observed comparing Example 11 to Examples 12-28. Without wishing to be bound to any particular theory, it is believed that the addition of lanthanum reduces the acidity of the support and thus disfavours the dehydration of ethanol to ethylene and consequently increases the selectivity to 1,3-butadiene. Furthermore, it is believed that lanthanum promotes the aldol condensation reaction between two molecules of acetaldehyde. In certain examples (15, 16 vs. 17), the addition of acetaldehyde to the feed has advantageous results in terms of selectivity towards 1,3-butadiene, Thus, not only can the by-product be recycled, this recycling also increases selectivity towards 1,3-butadiene. Increasing the temperature (see Examples 20 vs. 22; vs. 23; 24 vs. 26; 25 vs. 27) increases the conversion whilst having minimal effect of the selectivity to 1,3-butadiene+acetaldehyde.

The following paragraphs relate to preferred embodiments of the invention.

1. A process for the production of 1,3-butadiene, the process comprising
   i) providing a supported catalyst comprising lanthanum, zirconium, and zinc, the support comprising silica; and
   ii) contacting a feed comprising ethanol with the supported catalyst,
   to obtain a raw product comprising 1,3-butadiene.

2. The process according to para. 1, characterized in that contacting ii) takes place at a temperature in a range of 300 to 425° C.

3. The process according to para. 1 or para. 2, characterized in that contacting ii) takes place at a weight hourly space velocity of 0.2-7 h⁻¹.

4. The process according to any one of the preceding claims, characterized in that the feed additionally comprises acetaldehyde.

5. The process according to any one of the preceding paras., characterized in that it further comprises
   iii) separating the raw product into a first portion comprising 1,3-butadiene and a second portion comprising acetaldehyde.

6. The process according to para. 5, characterized in that at least part of the second portion is recycled into the feed.

7. The process according to any one of the preceding paras., characterized in that contacting ii) takes place in the presence of the supported catalyst according to para. 12.

8. A method for preparation of a supported catalyst, the method comprising:
   a) impregnating a support comprising silica with a salt of lanthanum;
   b) drying the impregnated support of step a); and
   c) calcining the dried impregnated support of step b); wherein the supported catalyst in addition to lanthanum comprises zirconium and zinc.

9. The method according to para. 8, characterized in that the method further comprises
   d) impregnating the calcined dried impregnated support of step c) with a salt of zirconium and a salt of zinc;
   e) drying the impregnated support of step d); and
   f) calcining the dried impregnated support of step e).

10. The method according to para. 8, characterized in that the support is impregnated in step a) with a salt of lanthanum, a salt of zirconium, and a salt of zinc.

11. Method according to any one of paras. 8 to 10, characterized in that the support is silica.

12. Supported catalyst produced or producible according to the method of any one of para. 8 to 11.

13. Use of lanthanum in a catalyst for the production of 1,3-butadiene from a feed comprising ethanol and optionally acetaldehyde, to increase the selectivity of the catalytic reaction to 1,3-butadiene.

The invention claimed is:

1. A process for the production of 1,3-butadiene, the process comprising
   i) providing a supported catalyst comprising lanthanum, zirconium, and zinc, wherein the support comprises silica; and
   ii) contacting a feed comprising ethanol with the supported catalyst to produce a raw product comprising 1,3-butadiene.

2. The process according to claim 1, wherein contacting ii) takes place at a temperature in a range of 300 to 425° C.

3. The process according to claim 1, wherein contacting ii) takes place at a weight hourly space velocity of 0.2-7 $h^{-1}$.

4. The process according to claim 1, wherein the feed further comprises acetaldehyde.

5. The process according to claim 1, further comprising
   iii) separating the raw product into a first portion comprising 1,3-butadiene and a second portion comprising acetaldehyde.

6. The process according to claim 5, wherein at least part of the second portion is recycled into the feed.

7. The process according to claim 1, wherein a process for producing the supported catalyst comprises:
   a) impregnating a support comprising silica with a salt of lanthanum, a salt of zirconium, and a salt of zinc;
   b) drying the impregnated support of step a); and
   c) calcining the dried impregnated support of step b).

8. The process according to claim 1, wherein a process for producing the supported catalyst comprises:
   a) impregnating a support comprising silica with a salt of lanthanum;
   b) drying the impregnated support of step a);
   c) calcining the dried impregnated support of step b);
   d) impregnating the calcined dried impregnated support of step c) with a salt of zirconium and a salt of zinc;
   e) drying the impregnated support of step d); and
   f) calcining the dried impregnated support of step e).

* * * * *